United States Patent
Euler et al.

(10) Patent No.: US 8,968,645 B2
(45) Date of Patent: Mar. 3, 2015

(54) BEVERAGE BOTTLING PLANT HAVING AN APPARATUS FOR THE TREATMENT OF BOTTLES OR SIMILAR CONTAINERS, AND A METHOD AND APPARATUS FOR THE TREATMENT OF BOTTLES OR SIMILAR CONTAINERS

(75) Inventors: Tobias Euler, Bad Kreuznach (DE); Detlef Mette, Bad Münster (DE); Jörg Beckmann, Stade (DE)

(73) Assignee: KHS GmbH, Dortmund (DE)

( * ) Notice: Subject to any disclaimer, the term of this patent is extended or adjusted under 35 U.S.C. 154(b) by 1294 days.

(21) Appl. No.: 12/274,575

(22) Filed: Nov. 20, 2008

(65) Prior Publication Data

US 2009/0130268 A1    May 21, 2009

Related U.S. Application Data

(63) Continuation-in-part of application No. PCT/EP2007/004434, filed on May 18, 2007.

(30) Foreign Application Priority Data

May 20, 2006  (DE) .......................... 10 2006 023 764

(51) Int. Cl.
*A61L 2/24*        (2006.01)
*A61L 2/00*        (2006.01)
(Continued)

(52) U.S. Cl.
CPC ............... *B67C 7/0073* (2013.01); *B67C 3/007* (2013.01); *A61L 2/22* (2013.01)
USPC .................. 422/3; 422/38; 426/407

(58) Field of Classification Search
CPC ................... A61L 2/22; B67C 7/0073

USPC ......................................... 422/3, 38; 426/407
See application file for complete search history.

(56) References Cited

U.S. PATENT DOCUMENTS 5,651,235 A * 7/1997 Ashley et al. ................... 53/458
6,024,917 A   2/2000 Kamstra
(Continued)

FOREIGN PATENT DOCUMENTS

DE      87 00 988       3/1987
DE      199 09 826 A1   9/2000
(Continued)

OTHER PUBLICATIONS

International Search Report PCT/EP2007/004434 and English translation thereof.

*Primary Examiner* — Kevin Joyner
(74) *Attorney, Agent, or Firm* — Nils H. Ljungman & Associates (57) ABSTRACT

Method and apparatus for treating containers, such as bottles, cans, or similar containers, by introducing at least one sterilization medium into a container when the container is at a first position on a movement path, and then stopping treatment when the container is at a second position on the movement path. A temperature of the container is then measured to determine if the measured container temperature lies within a predetermined range of temperature. If not, the length of the path between the first position and the second position is changed to thereby change the treatment procedure for subsequent containers, such that, after the subsequent containers have been treated according to the changed treatment procedure, the temperatures of the subsequent containers lie within the predetermined range of temperature.

20 Claims, 3 Drawing Sheets

(51) Int. Cl.
*A23L 3/10* (2006.01)
*B67C 3/00* (2006.01)
*A61L 2/22* (2006.01)
*B67C 7/00* (2006.01)

(56) References Cited

U.S. PATENT DOCUMENTS

2002/0159915 A1* 10/2002 Zelina et al. .................. 422/3
2004/0131519 A1* 7/2004 Amedeo et al. ............ 422/308
2004/0208781 A1 10/2004 Hayashi et al.

FOREIGN PATENT DOCUMENTS

| DE | 102 17 145 A1 | 10/2003 |
| DE | 103 55 183 | 6/2005 |
| EP | 0 334 288 | 9/1989 |
| FR | 2 576 003 | 7/1986 |
| JP | 9239009 A | 9/1997 |
| JP | 2006069643 A | 3/2006 |
| WO | WO 01/29528 | 4/2001 |

* cited by examiner

BEVERAGE BOTTLING PLANT HAVING AN APPARATUS FOR THE TREATMENT OF BOTTLES OR SIMILAR CONTAINERS, AND A METHOD AND APPARATUS FOR THE TREATMENT OF BOTTLES OR SIMILAR CONTAINERS

CONTINUING APPLICATION DATA

This application is a Continuation-In-Part application of International Patent Application No. PCT/EP2007/004434, filed on May 18, 2008, which claims priority from Federal Republic of Germany Patent Application No. 10 2006 023 764.1, filed on May 20, 2006. International Patent Application No. PCT/EP2007/004434 was pending as of the filing date of this application. The United States was an elected state in International Patent Application No. PCT/EP2007/004434.

BACKGROUND

1. Technical Field

The present application relates to a beverage bottling plant. The present application also relates to a method for the treatment of bottles or similar containers. The present application also relates to an apparatus for the treatment of bottles or similar containers.

2. Background Information

Background information is for informational purposes only and does not necessarily admit that subsequently mentioned information and publications are prior art.

Some methods for the treatment of bottles or similar containers involve treating with a heated medium and subsequent treatment with hot air. Each of the two treatment steps are performed on a treatment line of constant length at treatment stations arranged on the circumference of a powered rotor rotating around a vertical axis. The treated containers are then generally forwarded to a filling machine for the sterile or aseptic filling with a liquid product.

To monitor the success of the two-step treatment with a heated medium and hot air, the temperature of the container is measured at the end of each treatment line using a non-contact temperature sensor, for example. If the container temperature deviates excessively from a reference temperature, the respective container is removed and/or an alarm is annunciated and/or the treatment unit and downstream filling station are shut down.

The principle behind temperature monitoring is that sufficiently long treatment, and thus successful treatment, of the container with the heated treatment medium results in a certain container temperature. Disadvantageous is the fact that the effectiveness of treatment and thus the temperature of the containers are dependent on various parameters and variables, such as the type and size of the containers; machine speed, i.e. the number of treated containers per unit time; and the cool down process undergone by the containers during treatment, which process itself is dependent on a variety of in part random variables, including the ambient temperature, air flow, humidity, etc. For these reasons, the tolerance range for deviations of the container temperature measured at the end of the respective treatment line must be or should be relatively wide, e.g., on the scale of +/−twenty degrees Celsius.

OBJECT OR OBJECTS

The object of the present application which is believed to be the object at the time of filing is to demonstrate a method by means of which an improved monitoring of the treatment of bottles or similar containers with a treatment medium can be achieved. A method for achieving this object is disclosed as a method for the treatment of bottles or similar containers by the admission of at least one heated medium into the containers, which during the treatment are moved by means of at least one conveyor along at least one treatment line running from a start position and an end position for the initiation and termination of the treatment. The container temperature is measured after treatment using at least one temperature sensor, wherein the length of the at least one treatment line can be modified by open or closed-loop control action such that the measured container temperature corresponds at least within a specified tolerance range to a reference temperature.

An apparatus for performing the method is an apparatus for the treatment of bottles or similar containers by the admission of at least one heated medium into the containers, having at least one conveyor with which the containers are moved during the treatment on at least one treatment line running from a start position and an end position for the initiation and termination of the treatment. The device comprises at least one temperature sensor for measuring the container temperature following treatment, wherein a control unit, with which the length of the at least one treatment line can be modified by open or closed-loop control action such that the respective measured container temperature corresponds at least within a specified tolerance range to a reference temperature.

SUMMARY

In a general embodiment of the method according to the present application, in a complete reversal of the previous concepts, the respective start position at which the treatment is initiated is varied as a function of the temperature of the container measured at the end or immediately downstream, or generally downstream, of the treatment line to essentially lengthen or shorten the treatment line in at least one embodiment of the present application, with reference to a reference temperature that can be stored for different types and sizes of containers, for example, in the memory of an electronic measurement and control system. This is possible in a relatively simple manner by activating the treatment stations on the respective transport element or conveyor correspondingly.

In another general embodiment of the present application, the end position at which the respective treatment is terminated is shifted, again as a function of the temperature of the containers measured at the end of the treatment line or immediately downstream or generally downstream of the treatment line, again by essentially lengthening or shortening the treatment lines, in one possible embodiment, with reference to a reference temperature.

It is also possible to modify the treatment line by open or closed-loop control action on the basis of operating parameters such as the number of containers treated per unit time, ambient temperature, humidity, etc., and then measure the container temperature at the end of each treatment line solely for monitoring purposes.

It is also possible to set the end position at which the treatment is terminated on the basis of certain operating parameters, e.g., on the basis of the type and/or size of the containers, in which case the start position is varied by temperature control, i.e. by measuring the temperature of the containers and, in at least one possible embodiment of the present application, by comparing the measured temperature to a reference temperature and essentially lengthening or shortening the treatment line so that the measured temperature of the containers (actual value) corresponds exactly or substantially with the reference temperature (specified value), if possible.

The various methods for controlling and/or monitoring the treatment can also be combined.

The method according to the present application has the advantage that the treatment of the containers is independent of external variables, in at least one possible embodiment, independent of the machine speed (number of containers treated per unit time) and also independent of a container cooldown process determined by environmental influences, and that the influence of external factors, in at least one possible embodiment, of random, uncontrollable factors, on the treatment and/or its monitoring, such as ambient temperature, humidity, air flows, etc., is largely eliminated.

The above-discussed embodiments of the present invention will be described further hereinbelow. When the word "invention" or "embodiment of the invention" is used in this specification, the word "invention" or "embodiment of the invention" includes "inventions" or "embodiments of the invention", that is the plural of "invention" or "embodiment of the invention". By stating "invention" or "embodiment of the invention", the Applicant does not in any way admit that the present application does not include more than one patentably and non-obviously distinct invention, and maintains that this application may include more than one patentably and non-obviously distinct invention. The Applicant hereby asserts that the disclosure of this application may include more than one invention, and, in the event that there is more than one invention, that these inventions may be patentable and non-obvious one with respect to the other.

BRIEF DESCRIPTION OF THE DRAWINGS

Further embodiments of the present application are disclosed hereinbelow. One possible embodiment of the present application is described in greater detail below illustrated with the accompanying drawings, in which.

DESCRIPTION OF EMBODIMENT OR EMBODIMENTS

Figure 1:
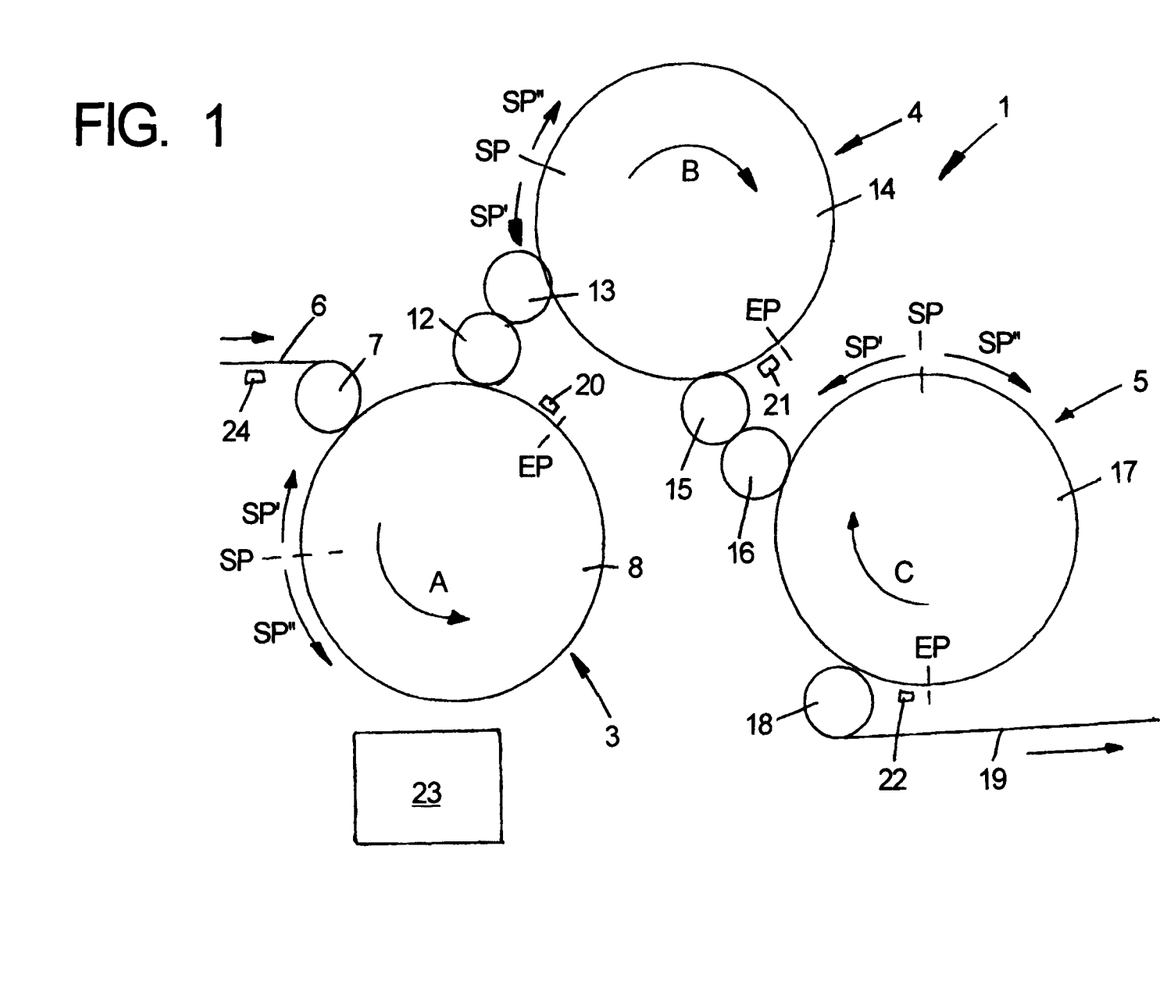
FIG. 1 shows a plan view of a very simplified representation of a machine for the treatment of bottles or similar containers, in one possible embodiment, for the cold aseptic filling of a liquid product such as fruit juices or milk, comprising a cleaner and two activators downstream of the cleaner.
Figure 1A:
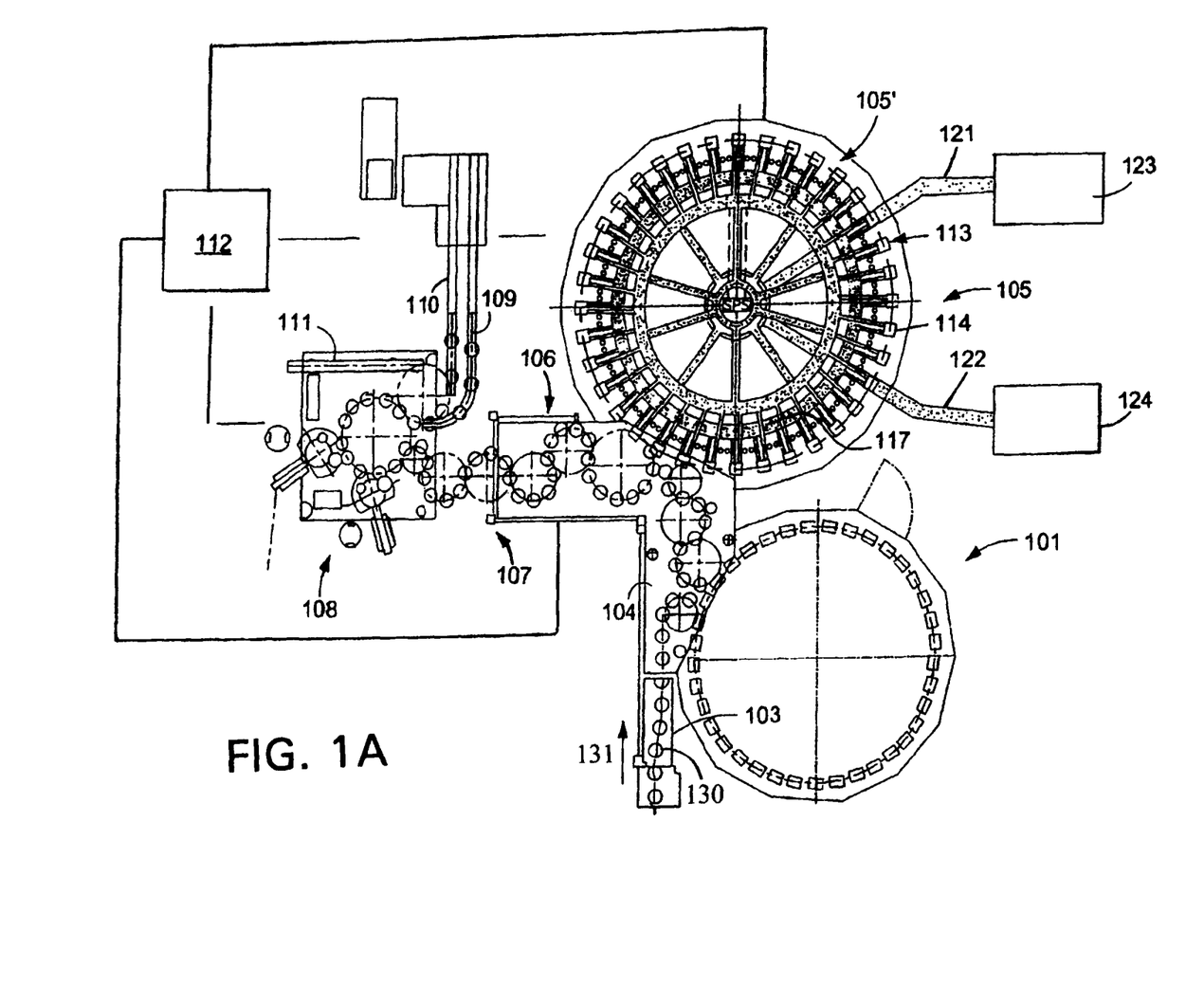
FIG. 1A is a schematic illustration of a container filling plant in accordance with one possible embodiment.

FIG. 1A shows schematically the main components of one possible embodiment example of a system for filling containers, specifically, a beverage bottling plant for filling bottles B with at least one liquid beverage, in accordance with at least one possible embodiment, in which system or plant could possibly be utilized at least one aspect, or several aspects, of the embodiments disclosed herein.

FIG. 1A shows a rinsing arrangement or rinsing station 101, to which the containers, namely bottles B, are fed in the direction of travel as indicated by the arrow A1, by a first conveyer arrangement 103, which can be a linear conveyor or a combination of a linear conveyor and a starwheel. Downstream of the rinsing arrangement or rinsing station 101, in the direction of travel as indicated by the arrow A1, the rinsed bottles B are transported to a beverage filling machine 105 by a second conveyer arrangement 104 that is formed, for example, by one or more starwheels that introduce bottles B into the beverage filling machine 105.

The beverage filling machine 105 shown is of a revolving or rotary design, with a rotor 105', which revolves around a central, vertical machine axis. The rotor 105' is designed to receive and hold the bottles B for filling at a plurality of filling positions 113 located about the periphery of the rotor 105'. At each of the filling positions 103 is located a filling arrangement 114 having at least one filling device, element, apparatus, or valve. The filling arrangements 114 are designed to introduce a predetermined volume or amount of liquid beverage into the interior of the bottles B to a predetermined or desired level.

The filling arrangements 114 receive the liquid beverage material from a toroidal or annular vessel 117, in which a supply of liquid beverage material is stored under pressure by a gas. The toroidal vessel 117 is a component, for example, of the revolving rotor 105'. The toroidal vessel 117 can be connected by means of a rotary coupling or a coupling that permits rotation. The toroidal vessel 117 is also connected to at least one external reservoir or supply of liquid beverage material by a conduit or supply line. In the embodiment shown in FIG. 1A, there are two external supply reservoirs 123 and 124, each of which is configured to store either the same liquid beverage product or different products. These reservoirs 123, 124 are connected to the toroidal or annular vessel 117 by corresponding supply lines, conduits, or arrangements 121 and 122. The external supply reservoirs 123, 124 could be in the form of simple storage tanks, or in the form of liquid beverage product mixers, in at least one possible embodiment.

As well as the more typical filling machines having one toroidal vessel, it is possible that in at least one possible embodiment there could be a second toroidal or annular vessel which contains a second product. In this case, each filling arrangement 114 could be connected by separate connections to each of the two toroidal vessels and have two individually-controllable fluid or control valves, so that in each bottle B, the first product or the second product can be filled by means of an appropriate control of the filling product or fluid valves.

Downstream of the beverage filling machine 105, in the direction of travel of the bottles B, there can be a beverage bottle closing arrangement or closing station 106 which closes or caps the bottles B. The beverage bottle closing arrangement or closing station 106 can be connected by a third conveyer arrangement 107 to a beverage bottle labeling arrangement or labeling station 108. The third conveyor arrangement may be formed, for example, by a plurality of starwheels, or may also include a linear conveyor device. In the illustrated embodiment, the beverage bottle labeling arrangement or labeling station 108 has at least one labeling unit, device, or module, for applying labels to bottles B. In the embodiment shown, the labeling arrangement 108 has three output conveyer arrangements: a first output conveyer arrangement 109, a second output conveyer arrangement 110, and a third output conveyer arrangement 111, all of which convey filled, closed, and labeled bottles B to different locations. In the event pre-labeled bottles are used, a beverage labeling station 108 would not necessarily be needed and could be omitted from the process of the beverage bottling plant.

The first output conveyer arrangement 109, in the embodiment shown, is designed to convey bottles B that are filled with a first type of liquid beverage supplied by, for example, the supply reservoir 123. The second output conveyer arrangement 110, in the embodiment shown, is designed to convey bottles B that are filled with a second type of liquid beverage supplied by, for example, the supply reservoir 124. The third output conveyer arrangement 111, in the embodiment shown, is designed to convey incorrectly labeled bottles B. To further explain, the labeling arrangement 108 can comprise at least one beverage bottle inspection or monitoring device that inspects or monitors the location of labels on the bottles B to determine if the labels have been correctly placed or aligned on the bottles B. The third output conveyer arrangement 111 removes any bottles B which have been incorrectly labeled as determined by the inspecting device.

The beverage bottling plant can be controlled by a central control arrangement 112, which could be, for example, computerized control system that monitors and controls the operation of the various stations and mechanisms of the beverage bottling plant.

The machine, designated as a whole in the Figures with 1, serves to treat the bottles 2 by the admission of a first, heated aerosol medium into the bottles and the subsequent treatment with hot air to activate the first medium and then blow it out of same. For this purpose, the machine is equipped with a cleaner/sterilizer, designated as a whole in FIG. 1 with 3 and in which the bottles 2 are impinged with the treatment medium; and two activators, designated in FIG. 1 with 4 and 5 and in which the bottles 2 are treated with hot air to activate and blow out or remove the treatment medium.

The sterilizer 3, into which the bottles 2 are admitted in a standing position, i.e. with the bottle axis oriented vertically, via a conveyor 6 and a starwheel 7 comprising the bottle inlet, essentially comprises a powered rotor 8 rotating around a vertical machine axis and having a plurality of treatment stations around its circumference. The individual bottles 2, which are passed one after another from the inlet starwheel 7 to a container carrier 9, are held by said carrier suspended by a flange 2.2 in the vicinity of the bottle mouth 2.1.

Figure 2:
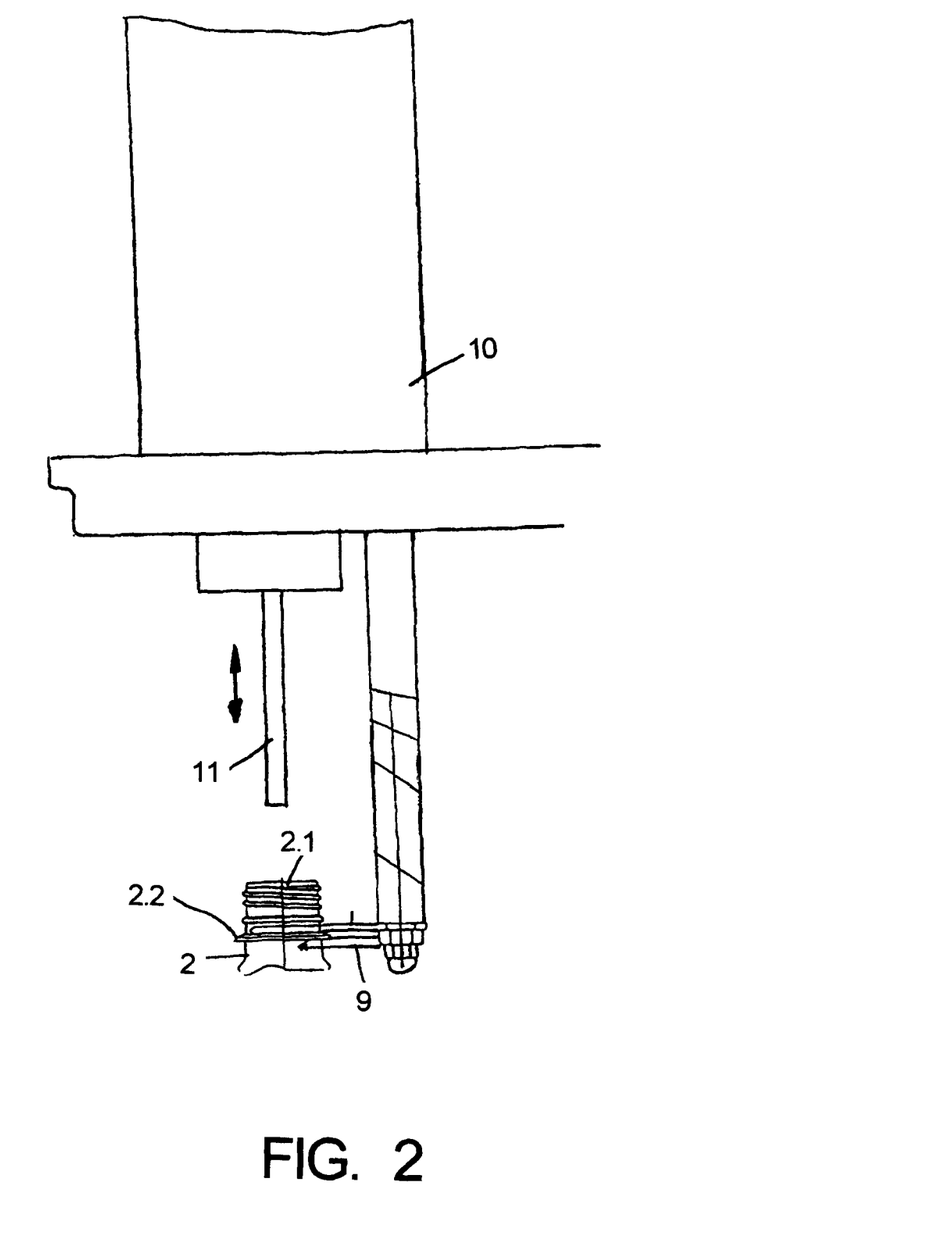
FIG. 2 shows a simplified representation of one of the treatment heads of the cleaner or the activators.

Each treatment head 10 has, among other things, a treatment tube 11, the open end of which can be inserted into the bottle 2 through the mouth 2.1 and from which the heated treatment medium is admitted into the interior of the respective bottle 2 during the treatment. Each of the bottles 2 impinged with the treatment medium are then transported via two powered, rotating starwheels 11 and 12, where starwheel 11 is the outlet starwheel of the sterilizer 3 and starwheel 12 is the inlet starwheel of the first activator 4, to a treatment station of this activator 4, which itself essentially comprises a powered rotor 13 rotating around a vertical axis. The treatment stations arranged around the circumference of this rotor 13 are configured in the same manner as the treatment stations of the sterilizer 3 described above, i.e. the treatment stations of the activator 4 also each comprise a container or bottle carrier 9 and a treatment head 10, although in the case of the activator 4 hot air is blown into the bottle 2 through the respective treatment tube 11 to activate the first heated aerosol medium, and also to blow out or blow dry the bottles 2. From the activator 4 or the treatment stations provided on the rotor 14 there, each of the bottles is passed to one of the treatment stations of the activator 5 via the starwheels 15 and 16, where starwheel 15 is the outlet starwheel of the activator 4 and starwheel 16 is the inlet starwheel of activator 5. This essentially comprises a powered rotor 17 rotating around a vertical axis and having around its circumference a plurality of treatment stations for receiving one bottle 2 each and admitting hot air into these bottles 2, likewise to activate the treatment medium or maintain this activation and/or to completely blow out or blow dry the bottles 2. The treated bottles 2 then pass via the outlet starwheel 18 to a conveyor 19, by means of which they are carried to a filling machine.

The direction of rotation of the rotors 8, 14, 17 is shown in FIG. 1 with the arrows A, B and C, respectively.

The treatment stations at the activators 4 and 5 or the rotors 14 and 17 there are configured in the same way as the treatment stations of the sterilizer 3 at rotor 8, i.e. the treatment stations each comprise a container carrier 9 and a treatment head 8, with the difference that with the activators 4 and 5, hot air is admitted into the bottles 2 via the treatment head or treatment tube 1.

To monitor the treatment process, temperature sensors 20, 21 and 22 are provided, each of which measures the temperature of the bottles without contact by means of the infrared radiation given off by the respective bottle 2 heated by the treatment medium. These sensors are realized as, or similar to, pyrometers, and are arranged along the line of motion of the bottles 2 but do not rotate with the rotor 8, 14 or 17, with the sensor 20 arranged at the outlet of the sterilizer 3; sensor 21 at the outlet of the activator 4; and sensor 22 at the outlet of the activator 5. The signals from the sensors 20 through 22 are fed to a central control and monitoring unit, which, among other things, controls the individual treatment stations of the sterilizer 3 and of the activators 4 and 5 or the treatment heads 10 located there. The electronic measurement and control unit compares the temperatures T1 (sensor 20), T2 (sensor 21) and T3 (sensor 22) measured by the sensors 20 through 22 to the reference temperatures stored in its memory for the respective bottle type and/or shape and derives control signals for controlling the treatment heads 10 from this information. The reference values for the temperatures T1 through T3 are, for example:

$T1_{Ref}$: forty-five degrees Celsius
$T2_{Ref}$: fifty-five degrees Celsius
$T3_{Ref}$: sixty-five degrees Celsius The respective temperature measured at the sensors 20 through 22 is not only a function of the respective energy input that occurred with the admission of the treatment medium into the bottles 2, but also of additional parameters. These additional parameters include bottle size and/or bottle type, and the amount of time the respective bottle 2 is treated with the respective treatment medium. Cooling of the bottle 2 during treatment, i.e. the amount of heat given off by the respective bottle to the environment during treatment, also influences the temperature measured at the sensors 20 through 22. As conducted here, cooling itself is a function of various variables.

To reach the respective reference temperature for the temperatures T1 through T3, the electronic measurement and control unit 23 modifies by control action the start position SP at which the respective treatment with the treatment medium is initiated accordingly so that the treatment line, i.e. the angle area of the rotary movement of the rotor 8, 14 or 17 between the start position SP and the end position EP at which the treatment with the treatment medium is terminated and at which in the embodiment shown here the respective sensor 20, 21 or 22 is located, is modified such that the measured temperatures T1 through T3 correspond as closely as possible to the respective reference temperatures $T1_{Ref}$, $T2_{Ref}$ and $T3_{Ref}$. Possibly, this means that with increasing performance of the machine 1, the respective start position SP is shifted opposite the direction of rotation A, B or C in the direction of the bottle or container inlet 7, 13 or 16 to essentially lengthen the treatment line, as is indicated in FIG. 1 by the arrow SP'. Conversely, with reduced performance of the machine 1, the start position SP is shifted in the direction of rotation of the rotor A, B or C to essentially shorten the treatment line, as is indicated in FIG. 1 with the arrow SP".

The treatment of the bottles 2 with the respective treatment medium is terminated at the respective end position EP, i.e. at the measuring position at which the sensors 20, 21 or 22 are also located, or in the direction of rotation of the rotor 8, 14 or 17 shortly before reaching this measuring position.

This temperature-controlled lengthening or shortening of the treatment line also takes into consideration the other variables indicated above in addition to the performance of the machine. For example, the start position SP is shifted as function of such things as the cooling of the bottles 2 during treatment or the ambient temperature, but also of the bottle type and size or the heat capacity of the treated bottles 2, i.e. with bottles 2 that are difficult to heat, i.e. bottles 2 with a high heat capacity, the start position SP is shifted in the direction of the arrow SP', and with bottles 2 that are easy to heat, i.e. bottles 2 with a low heat capacity, the shift is in the direction of the arrow SP".

Such bottles 2, for which the temperature measured by the respective sensor 20, 21 or 22 deviates significantly or relatively from the respective reference temperature, and in one possible embodiment is significantly below or relatively below the reference temperature, are removed at a suitable position as insufficiently treated or cleaned bottles, in at least one possible embodiment already at the sterilizer 3 or at the activator 4 or 5.

The present application was described above with reference to one exemplary embodiment. It will be understood that numerous modifications and derivations are possible without departing from the teaching on which the present application is based.

For example, it is also possible to shift the end position of the respective treatment as a function of temperature to achieve a temperature-controlled lengthening or shortening of the respective treatment line.

Another possibility is to lengthen or shorten the treatment line, i.e. to shift the start SP and/or end position EP by means of open or closed-loop control as a function of the current machine speed of the machine.

It is also possible to set the end position EP of the respective treatment or treatment line as a function of definable operating parameters and to shift the start position SP by means of temperature and/or speed control.

It is possible in at least one embodiment for the respective measuring point for the temperature measurement to also be shifted when changing or setting the end position EP. This can be done, for example, by mechanically moving the temperature sensor on a circular track around the axis of the respective rotor 8, 14 or 17, or the measuring point can be shifted by arranging multiple temperature sensors in sequence along the line of motion of the treatment stations and, as a function of the change or setting of the end position EP, only or possibly only the measurement signal of temperature sensor corresponding to this end position is considered, i.e. by selecting the temperature sensor corresponding to this end position.

The various methods for open and/or closed-loop control and monitoring can also be used in combination.

It is also possible to provide an additional temperature sensor 24 at the bottle inlet to the machine 1 to measure the initial temperature T0 of the bottles 2, which temperature T0 is then used as an additional control and/or monitoring parameter, e.g., for determining corresponding reference temperatures, etc.

It was also assumed above that the machine 1 for the treatment of bottles 2 have a flange 2.2 in the vicinity of their mouth 2.1. With appropriately configured bottle or container holders 9, the machine 1 can, of course, also be used for other types of bottles and in one possible embodiment for a wide variety of containers in general.

The present application relates to an apparatus for the treatment of bottles or similar containers by the admission of a heated treatment medium into the respective containers arranged in the treatment station of a conveyor and moved with said conveyer on a transport line, on which line the initiation and termination of treatment with the treatment medium take place between at least one start position and one end position and on which the temperature of the respective containers is measured by at least one temperature sensor following the at least one treatment.

One feature or aspect of an embodiment is believed at the time of the filing of this patent application to possibly reside broadly in a method for the treatment of bottles or similar containers 2 by the admission of at least one heated medium into the containers 2, which during the treatment are moved by means of at least one conveyor 8, 14, 17 along at least one treatment line running from a start position SP and an end position EP for the initiation and termination of the treatment, whereby the container temperature is measured after treatment using at least one temperature sensor 20, 21, 22, 22', wherein the length of the at least one treatment line can be modified by open or closed-loop control action such that the measured container temperature T1, T2, T3 corresponds at least within a specified tolerance range to a reference temperature $T1_{Ref}$, $T2_{Ref}$, $T3_{Ref}$.

Another feature or aspect of an embodiment is believed at the time of the filing of this patent application to possibly reside broadly in the method, wherein the length of the at least one treatment line can be modified by open or closed-loop temperature control, for example by comparing the measured container temperature as the actual value to the reference temperature $T1_{Ref}$, $T2_{Ref}$, $T3_{Ref}$.

Yet another feature or aspect of an embodiment is believed at the time of the filing of this patent application to possibly reside broadly in the method, wherein the length of the at least one treatment line can be modified as a function of operating parameters, for example as a function of the number of containers 2 treated per unit time (machine speed) and/or the type and/or size of the containers and/or the ambient temperature and/or moisture.

Still another feature or aspect of an embodiment is believed at the time of the filing of this patent application to possibly reside broadly in the method, wherein the respective treatment line is modified by modifying its start position SP.

A further feature or aspect of an embodiment is believed at the time of the filing of this patent application to possibly reside broadly in the method, wherein the respective treatment lines are modified by modifying their end position EP.

Another feature or aspect of an embodiment is believed at the time of the filing of this patent application to possibly reside broadly in the method, wherein, with the end position EP set on the basis of operating parameters, the start position is modified by temperature control.

Yet another feature or aspect of an embodiment is believed at the time of the filing of this patent application to possibly reside broadly in the method, wherein, with the start position SP set on the basis of operating parameters, the end position EP is modified by temperature control.

Still another feature or aspect of an embodiment is believed at the time of the filing of this patent application to possibly reside broadly in the method, wherein the container temperature T1, T2, T3 is measured either at the end of the respective treatment line or immediately downstream of the treatment line.

A further feature or aspect of an embodiment is believed at the time of the filing of this patent application to possibly reside broadly in the method, wherein at least two treatment lines are arranged sequentially along a transport line and in the direction of transport of the containers 2, and that the length of at least one treatment line can be modified by temperature control and/or as a function of operating parameters.

Another feature or aspect of an embodiment is believed at the time of the filing of this patent application to possibly reside broadly in the method, wherein the temperature T1, T2, T3 of the containers 2 is measured at the end of each treatment line and or downstream of the each treatment line.

Yet another feature or aspect of an embodiment is believed at the time of the filing of this patent application to possibly reside broadly in the method, including the use of multiple conveyors 8, 14, 17, each of which forms at least one treatment line, arranged in sequence in the direction of transport to form the transport line.

One feature or aspect of an embodiment is believed at the time of the filing of this patent application to possibly reside broadly in the method, wherein the containers 2 are treated on at least one treatment line 8 with a heated medium containing hydrogen peroxide $H_2O_2$, in one possible embodiment of the present application, in the form of an aerosol, and with hot air on at least one subsequent treatment line 14, 17 in the direction of transport.

Another feature or aspect of an embodiment is believed at the time of the filing of this patent application to possibly reside broadly in the method, including the use of at least one temperature sensor 20, 21, 22, 22' associated with the respective treatment line for the often non-contact (or contactless) measurement of the temperature of the respective container 2 moved past the temperature sensor.

Yet another feature or aspect of an embodiment is believed at the time of the filing of this patent application to possibly reside broadly in the method, including the use of at least one of the pyrometers or infrared thermometers associated with the at least one treatment line as a temperature sensor 20, 21, 22, 22'.

Still another feature or aspect of an embodiment is believed at the time of the filing of this patent application to possibly reside broadly in the method, wherein the at least one conveyor 8, 14, 17 has multiple treatment stations for receiving one container 2 each.

A further feature or aspect of an embodiment is believed at the time of the filing of this patent application to possibly reside broadly in the method, wherein the at least one conveyor is a powered rotor 8, 14, 17 rotating around a vertical axis and having multiple treatment stations around its circumference, and that the treatment line is formed by an angle area of the rotary motion of the rotor 8, 14, 17.

Another feature or aspect of an embodiment is believed at the time of the filing of this patent application to possibly reside broadly in the method, wherein the treatment stations each comprise a container carrier 9 and a treatment head 10, which are controlled by a measurement and control unit 23 as a function of the actual measured temperature of the container T1, T2, T3 and the reference temperature.

Yet another feature or aspect of an embodiment is believed at the time of the filing of this patent application to possibly reside broadly in the method, including the use of a transport line with three treatment lines arranged in sequence in the direction of transport of the containers 2, of which a first treatment line is for treatment with the medium containing hydrogen peroxide and the two subsequent treatment lines are for treatment with hot air.

Still another feature or aspect of an embodiment is believed at the time of the filing of this patent application to possibly reside broadly in the method, wherein each treatment line is formed by one transport element 8, 14, 17.

A further feature or aspect of an embodiment is believed at the time of the filing of this patent application to possibly reside broadly in an apparatus for the treatment of bottles or similar containers 2 by the admission of at least one heated medium into the containers 2, having at least one conveyor 8, 14, 17 with which the containers 2 are moved during the treatment on at least one treatment line running from a start position SP and an end position EP for the initiation and termination of the treatment, having at least one temperature sensor 20, 21, 22, 22' for measuring the container temperature following treatment, wherein a control unit 23, with which the length of the at least one treatment line can be modified by open or closed-loop control action such that the respective measured container temperature T1, T2, T3 corresponds at least within a specified tolerance range to a reference temperature $T1_{Ref}$, $T2_{Ref}$, $T3_{Ref}$.

Another feature or aspect of an embodiment is believed at the time of the filing of this patent application to possibly reside broadly in the apparatus, wherein the control unit 23 modifies the length of the at least one treatment line by open or closed-loop temperature control, for example by comparing the measured container temperature as the actual value to the reference temperature $T1_{Ref}$, $T2_{Ref}$, $T3_{Ref}$.

Yet another feature or aspect of an embodiment is believed at the time of the filing of this patent application to possibly reside broadly in the apparatus, wherein the control unit 23 modifies the length of the at least one treatment line as a function of operating parameters, for example as a function of the number of containers 2 treated per unit time (machine speed) and/or the type and/or size of the container and/or the ambient temperature and/or moisture.

Still another feature or aspect of an embodiment is believed at the time of the filing of this patent application to possibly reside broadly in the apparatus, wherein control unit 23 modifies the respective treatment line by modifying its start position SP.

A further feature or aspect of an embodiment is believed at the time of the filing of this patent application to possibly reside broadly in the apparatus, wherein the control unit 23 modifies the respective treatment line by modifying its end position EP.

Another feature or aspect of an embodiment is believed at the time of the filing of this patent application to possibly reside broadly in the apparatus, wherein, with the end position EP set on the basis of operating parameters, the control unit 23 modifies the start position by temperature control.

Yet another feature or aspect of an embodiment is believed at the time of the filing of this patent application to possibly reside broadly in the apparatus, wherein, with the start position SP set on the basis of operating parameters, the control unit 23 modifies the end position EP by temperature control.

One feature or aspect of an embodiment is believed at the time of the filing of this patent application to possibly reside broadly in the apparatus, wherein the sensors 20, 21, 22 for measuring the container temperature T1, T2, T3 are arranged either at the end of the respective treatment line or immediately downstream of the treatment line.

Another feature or aspect of an embodiment is believed at the time of the filing of this patent application to possibly reside broadly in the apparatus, wherein at least two treatment lines are arranged sequentially along a transport line and in the direction of transport of the containers 2, and that the control unit 23 modifies the length of at least one treatment line by temperature control and/or as a function of operating parameters.

Yet another feature or aspect of an embodiment is believed at the time of the filing of this patent application to possibly reside broadly in the apparatus, wherein at least one sensor 20, 21, 22 for measuring the temperature T1, T2, T3 of the containers 2 is arranged at the end or downstream of each treatment line.

Still another feature or aspect of an embodiment is believed at the time of the filing of this patent application to possibly reside broadly in the apparatus, wherein the transport line comprises multiple conveyors 8, 14, 17 arranged in sequence in the direction of transport, each of which forms at least one treatment line.

A further feature or aspect of an embodiment is believed at the time of the filing of this patent application to possibly reside broadly in the apparatus, comprising at least one temperature sensor 20, 21, 22, 22' associated with the respective treatment line for the often non-contact measurement of the temperature of the respective container 2 moved past the temperature sensor.

Another feature or aspect of an embodiment is believed at the time of the filing of this patent application to possibly reside broadly in the apparatus, comprising at least one pyrometer or infrared thermometer associated with the at least one treatment line as the temperature sensor 20, 21, 22, 22'. Some exam-examples of pyrometers which may possibly be used in at least one possible embodiment of the present application may possibly be those manufactured and sold by Omega Engineering Inc., 1 Omega Drive, Stamford, Conn. Still other devices which may possibly be used in at least one possible embodiment of the present application may possibly include the optical pyrometer types disclosed in: Hartel U.S. Pat. No. 5,398,734 (KHS Machinen-und Anlagenban Aktiengesellschaft); Green U.S. Pat. No. 3,535,522 (Glass Container Industry Research) and Howell U.S. Pat. Nos. 2,987,589 and 2,869,369 (Servo Corp. of America), the disclosures of which are all hereby incorporated by reference as if set forth in their entirety herein. Some examples of infrared thermometers which may possibly be used in at least one possible embodiment of the present application may possibly be found in the following US patents: Heinke et al. U.S. Pat. No. 5,81,410, and Christol et al. U.S. Pat. No. 4,634,294 (both assigned to Raytek, Inc.), the disclosures of which are also all hereby incorporated by reference as if set forth in their entirety herein.

The purpose of incorporating U.S. patents, Foreign patents, publications, etc. is solely to provide additional information relating to technical features of one or more embodiments, which information may not be completely disclosed in the wording in the pages of this application. Words relating to the opinions and judgments of the author and not directly relating to the technical details of the description of the embodiments therein are not incorporated by reference. The words all, always, absolutely, consistently, preferably, guarantee, particularly, constantly, ensure, necessarily, immediately, endlessly, avoid, exactly, continually, expediently, need, must, only, perpetual, precise, perfect, require, requisite, simultaneous, total, unavoidable, and unnecessary, or words substantially equivalent to the above-mentioned words in this sentence, when not used to describe technical features of one or more embodiments, are not considered to be incorporated by reference herein.

Yet another feature or aspect of an embodiment is believed at the time of the filing of this patent application to possibly reside broadly in the apparatus, wherein the at least one conveyor 8, 14, 17 has multiple treatment stations for receiving one container 2 each.

Still another feature or aspect of an embodiment is believed at the time of the filing of this patent application to possibly reside broadly in the apparatus, wherein the at least one conveyor is a powered rotor 8, 14, 17 rotating around a vertical axis and having multiple treatment stations around its circumference, and that the treatment line is formed by an angle area of the rotary motion of the rotor 8, 14, 17.

A further feature or aspect of an embodiment is believed at the time of the filing of this patent application to possibly reside broadly in the apparatus, wherein the treatment stations each comprise a container carrier 9 and a treatment head 10, which are controlled by a measurement and control unit 23 as a function of the actual measured temperature of the container T1, T2, T3 and the reference temperature.

Another feature or aspect of an embodiment is believed at the time of the filing of this patent application to possibly reside broadly in the apparatus, comprising a transport line with three treatment lines arranged in sequence in the direction of transport of the containers 2, of which a first treatment line is for treatment with the medium containing hydrogen peroxide and the two subsequent treatment lines are for treatment with hot air.

Yet another feature or aspect of an embodiment is believed at the time of the filing of this patent application to possibly reside broadly in the apparatus, wherein each treatment line is formed by one transport element 8, 14, 17.

One feature or aspect of an embodiment is believed at the time of the filing of this patent application to possibly reside broadly in in a beverage bottling plant for filling beverage bottles with liquid beverage materials, a method of operating a bottle treatment machine, said beverage bottling plant comprising: a beverage bottle cleaning machine comprising: at least one conveyor with which bottles are moved on at least one treatment line running from a start position to an end position for a length of treatment; at least one sensor for measuring a temperature associated with the bottle following the treatment; and a control unit for modifying the length of said treatment line when the measured bottle temperature falls outside a specified tolerance range for a reference temperature; said beverage bottling plant further comprising: a first conveyer arrangement being configured and disposed to move beverage bottles from said beverage bottle cleaning machine into a rotary liquid beverage bottle filling machine; said first conveyer arrangement comprising a star wheel structure; a beverage bottle closing machine being configured and disposed to close tops of filled liquid beverage bottles; a second conveyer arrangement being configured and disposed to move filled liquid beverage bottles from said liquid beverage filling machine into said liquid beverage bottle closing machine; said second conveyer arrangement comprising a star wheel structure; a beverage bottle labeling machine being configured and disposed to label filled, closed liquid beverage bottles; a third conveyor arrangement being configured and disposed to move filled, closed liquid beverage bottles from said liquid beverage bottle closing machine into said liquid beverage bottle labeling machine; said third conveyer arrangement comprising a star wheel structure; a liquid beverage bottle packing station being configured and disposed to package labeled, filled, closed liquid beverage bottles; a fourth conveyor arrangement being configured and disposed to move labeled, filled, closed liquid beverage bottles from said liquid beverage bottle labeling machine to said liquid beverage bottle packing station; and said fourth conveyer arrangement comprising a linear conveyor structure being configured and disposed to arrange liquid beverage bottles in groups for packing; said method of operating a bottle treatment machine comprising: (a) moving the bottles with at least one conveyor along at least one treatment line from a start position to an end position to effect an initial treatment which comprises injecting or spraying the heated medium into the containers; (b) measuring at least one temperature associated with said containers after said initial treatment with at least one temperature sensor to obtain at least one temperature; (c) comparing the measured temperature against a specified tolerance range for at least one reference temperature; and (d) modifying the length of the at least one treatment until the at least one measured temperature falls within the specified tolerance range for the at least one reference temperature and thus treating the containers subsequent to said modifying; (e) modifying said injection or spraying of said heated medium into said containers; and (f) treating said containers.

Another feature or aspect of an embodiment is believed at the time of the filing of this patent application to possibly reside broadly in the beverage bottling plant operating method, wherein the control unit of the beverage bottle cleaning machine modifies the treatment line length on the at least one conveyor by temperature control.

Still another feature or aspect of an embodiment is believed at the time of the filing of this patent application to possibly reside broadly in the beverage bottling plant operating method, wherein the control unit of the beverage bottle cleaning machine modifies the treatment line length as a function of at least one operating parameter selected from the group consisting of: the number of bottles treated per unit time (machine speed); the type and/or size of the bottles; ambient temperature; and moisture.

Yet another feature or aspect of an embodiment is believed at the time of the filing of this patent application to possibly reside broadly in the beverage bottling plant operating method, wherein the control unit of the beverage bottle cleaning machine modifies the treatment line length by modifying the start position.

A further feature or aspect of an embodiment is believed at the time of the filing of this patent application to possibly reside broadly in the beverage bottling plant operating method, wherein: the bottle temperature is measured at the end or immediately downstream of the treatment; and the control unit of the beverage bottle cleaning machine modifies the treatment line length by modifying the end position as a function of one or more operating parameters selected from the group consisting of: the number of bottles treated per unit time (machine speed); the bottle type; the bottle size; ambient temperature; and ambient moisture level.

One feature or aspect of an embodiment is believed at the time of the filing of this patent application to possibly reside broadly in a method for sterilizing bottles or similar containers with at least one heated sterilization medium, said method comprising: (a) moving the containers with at least one conveyor along at least one treatment line from a start position to an end position to effect an initial sterilization treatment which comprises injecting or spraying the heated sterilization medium into the containers; (b) measuring at least one temperature associated with said containers after said initial sterilization treatment with at least one temperature sensor to obtain at least one temperature; (c) comparing the measured temperature against a specified tolerance range for at least one reference temperature; (d) modifying the length of the at least one treatment until the at least one measured temperature falls within the specified tolerance range for the at least one reference temperature and thus sterilizing the containers subsequent to said modifying; and (e) modifying said injection or spraying of said heated sterilization medium into said containers.

Another feature or aspect of an embodiment is believed at the time of the filing of this patent application to possibly reside broadly in the method, which further comprises after step (d): suspending measurement of the at least one temperature for a predetermined period of time, said period of time being sufficiently short to minimize the effect of ambient conditions from drifting outside the at least one specified tolerance range; and continuing to treat the containers on the at least one conveyor for the modified treatment length.

Yet another feature or aspect of an embodiment is believed at the time of the filing of this patent application to possibly reside broadly in the method, which further comprises after step (d): wherein said period of time being sufficiently long to permit use of a computer with a minimal computational speed to perform calculations relating to said at least one temperature for determining said modifying injection or spraying of said sterilization medium and providing open loop or quasi open loop operation.

Still another feature or aspect of an embodiment is believed at the time of the filing of this patent application to possibly reside broadly in the method, which further comprises after step (d): measuring at least one temperature at bottles at a period of time substantially shorter than a period of time being sufficiently short to minimize the effect of ambient conditions from drifting outside the at least one specified tolerance range and modifying said injection or spraying to provide closed loop operation.

A further feature or aspect of an embodiment is believed at the time of the filing of this patent application to possibly reside broadly in the method, wherein comparing step (c) comprises: after the predetermined period of time, resuming measurement of the at least one temperature; and remodifying the length of the at least one treatment based on the resumed temperature measurement.

Another feature or aspect of an embodiment is believed at the time of the filing of this patent application to possibly reside broadly in the method, wherein modifying step (d) comprises: modifying the length of the at least one treatment on the at least one conveyor as a function of one or more operating parameters selected from the group consisting of: the number of containers treated per unit time (machine speed); the container type; the container size; ambient temperature; and ambient moisture level.

Still another feature or aspect of an embodiment is believed at the time of the filing of this patent application to possibly reside broadly in the method, wherein modifying step (d) comprises at least one of: modifying the start position; and modifying the end position.

Yet another feature or aspect of an embodiment is believed at the time of the filing of this patent application to possibly reside broadly in the method, which comprises: setting the end position on the basis of said operating parameters; and modifying the start position by said temperature control.

A further feature or aspect of an embodiment is believed at the time of the filing of this patent application to possibly reside broadly in the method, which comprises: setting the start position on the basis of operating parameters; and modifying the end position by temperature control.

Another feature or aspect of an embodiment is believed at the time of the filing of this patent application to possibly reside broadly in the method, which further comprises one of (a), (b) and (c): (a) measuring the container temperature at the end or immediately downstream of the treatment; (b) measuring the container temperature at the end or immediately downstream of the treatment; providing at least two treatment lines, arranged sequentially, in the direction of container transport; and modifying the length of at least one treatment line by one or more of temperature control; and as a function of operating parameters; and (c) measuring the container temperature at the end or immediately downstream of the treatment; providing at least two treatment lines, arranged sequentially, in the direction of container transport; modifying the length of at least one treatment line by one or more of temperature control; and as a function of operating parameters; and providing at least one treatment line with multiple conveyors sequentially arranged in the direction of container transport.

Still another feature or aspect of an embodiment is believed at the time of the filing of this patent application to possibly reside broadly in the method, wherein: for at least one treatment line, the heated medium contains hydrogen peroxide; and for at least one subsequent treatment line, the heated medium comprises hot air.

Yet another feature or aspect of an embodiment is believed at the time of the filing of this patent application to possibly reside broadly in the method, wherein measuring step (b) comprises: measuring the temperature of the container as it moves past a non-contacting temperature sensor.

A further feature or aspect of an embodiment is believed at the time of the filing of this patent application to possibly reside broadly in the method, wherein the non-contacting temperature sensor comprises at least one pyrometer or infrared thermometer.

Another feature or aspect of an embodiment is believed at the time of the filing of this patent application to possibly reside broadly in the method, wherein the method further comprises of one of (a), (b), and (c): (a) at least one conveyor has multiple treatment stations for receiving one container each; (b) at least one conveyor has multiple treatment stations for receiving one container each; and the at least one conveyor is a rotor that rotates around a vertical axis, said rotor having multiple treatment stations around its circumference with the treatment line being formed by an area of motion of the rotor; (c) at least one conveyor has multiple treatment stations for receiving one container each; the at least one conveyor is a rotor that rotates around a vertical axis, said rotor having multiple treatment stations around its circumference with the treatment line being formed by an area of motion of the rotor; and each treatment station comprises: a container carrier and a treatment head, both of which are controlled by a measurement and control unit as a function of the actual measured container temperature and the reference temperature.

Still another feature or aspect of an embodiment is believed at the time of the filing of this patent application to possibly reside broadly in the method, which uses a transport line with three treatment lines arranged in sequence in the direction of container transport, a first of said treatment lines using a medium containing hydrogen peroxide and two subsequent treatment lines using hot air.

One feature or aspect of an embodiment is believed at the time of the filing of this patent application to possibly reside broadly in an apparatus for the treatment of bottles or similar containers with at least one heated medium, said apparatus comprising: at least one conveyor with which the containers are moved on at least one treatment running from a start position to an end position for a length of treatment; at least one sensor for measuring a temperature associated with the container temperature following the treatment; a control unit for modifying the length of the treatment when the measured container temperature does not fall within a specified tolerance range for a reference temperature.

Another feature or aspect of an embodiment is believed at the time of the filing of this patent application to possibly reside broadly in the apparatus, wherein the control unit modifies the treatment length on the at least one conveyor by temperature control.

Still another feature or aspect of an embodiment is believed at the time of the filing of this patent application to possibly reside broadly in the apparatus, wherein the control unit modifies the treatment length as a function of at least one operating parameter selected from the group consisting of: the number of containers treated per unit time (machine speed); the type and/or size of the container; ambient temperature; and moisture.

Yet another feature or aspect of an embodiment is believed at the time of the filing of this patent application to possibly reside broadly in the apparatus, wherein the control unit modifies at least one of: the start position; and the end position.

A further feature or aspect of an embodiment is believed at the time of the filing of this patent application to possibly reside broadly in the apparatus, wherein the end position is set based on operating parameters and the control unit modifies the start position by temperature control.

Another feature or aspect of an embodiment is believed at the time of the filing of this patent application to possibly reside broadly in the apparatus, wherein: the start position is set based on operating parameters; and the control unit modifies the end position by temperature control.

Still another feature or aspect of an embodiment is believed at the time of the filing of this patent application to possibly reside broadly in the apparatus, which further comprises one of (a), (b) and (c): (a) wherein the sensor for measuring the container temperature is arranged at the end, or immediately downstream, of the treatment; (b) wherein the sensor for measuring the container temperature is arranged at the end, or immediately downstream, of the treatment; and at least two treatment lines are arranged sequentially along a transport line in the direction of container transport with the control unit modifying the treatment length by at least one of temperature control; and as a function of operating parameters; and (c) wherein the sensor for measuring the container temperature is arranged at the end, or immediately downstream, of the treatment; at least two treatment lines are arranged sequentially along a transport line in the direction of container transport with the control unit modifying the treatment length by at least one of temperature control; and as a function of operating parameters; and the transport line comprises multiple conveyors sequentially arranged in the direction of container transport, each conveyor forming at least one treatment line.

Yet another feature or aspect of an embodiment is believed at the time of the filing of this patent application to possibly reside broadly in the apparatus, wherein the at least one temperature sensor contactlessly measures temperature as the container moves past it.

A further feature or aspect of an embodiment is believed at the time of the filing of this patent application to possibly reside broadly in the apparatus, wherein the measuring sensor comprises: at least one pyrometer or infrared thermometer.

Another feature or aspect of an embodiment is believed at the time of the filing of this patent application to possibly reside broadly in the apparatus, which comprises one of (a), (b) and (c): (a) wherein the at least one conveyor has multiple treatment stations for receiving one container each; (b) wherein the at least one conveyor has multiple treatment stations for receiving one container each; the at least one conveyor is a rotor rotating around a vertical axis, said rotor having multiple treatment stations around its circumference; and a path of the treatment is in an area of rotary motion of the rotor; and (c) wherein the at least one conveyor has multiple treatment stations for receiving one container each; the at least one conveyor is a rotor rotating around a vertical axis, said rotor having multiple treatment stations around its circumference; a path of the treatment is in an area of rotary motion of the rotor; and each treatment station comprises a container carrier and a treatment head, both of which are controlled by a measurement and control unit as a function of the measured container temperature and the reference temperature.

Still another feature or aspect of an embodiment is believed at the time of the filing of this patent application to possibly reside broadly in the apparatus, wherein a transport line comprises three treatment lines sequentially arranged in the direction of container transport, a first line being for treatment with a medium containing hydrogen peroxide, and the two subsequent lines being for treatment with hot air.

Yet another feature or aspect of an embodiment is believed at the time of the filing of this patent application to possibly reside broadly in the apparatus, wherein each treatment line comprises one transport element.

The components disclosed in the various publications, disclosed or incorporated by reference herein, may possibly be used in possible embodiments of the present invention, as well as equivalents thereof.

The purpose of the statements about the technical field is generally to enable the Patent and Trademark Office and the public to determine quickly, from a cursory inspection, the nature of this patent application. The description of the technical field is believed, at the time of the filing of this patent application, to adequately describe the technical field of this patent application. However, the description of the technical field may not be completely applicable to the claims as originally filed in this patent application, as amended during prosecution of this patent application, and as ultimately allowed in any patent issuing from this patent application. Therefore, any statements made relating to the technical field are not intended to limit the claims in any manner and should not be interpreted as limiting the claims in any manner.

The appended drawings in their entirety, including all dimensions, proportions and/or shapes in at least one embodiment of the invention, are accurate and are hereby included by reference into this specification.

The background information is believed, at the time of the filing of this patent application, to adequately provide background information for this patent application. However, the background information may not be completely applicable to the claims as originally filed in this patent application, as amended during prosecution of this patent application, and as ultimately allowed in any patent issuing from this patent application. Therefore, any statements made relating to the background information are not intended to limit the claims in any manner and should not be interpreted as limiting the claims in any manner.

All, or substantially all, of the components and methods of the various embodiments may be used with at least one embodiment or all of the embodiments, if more than one embodiment is described herein.

The purpose of the statements about the object or objects is generally to enable the Patent and Trademark Office and the public to determine quickly, from a cursory inspection, the nature of this patent application. The description of the object or objects is believed, at the time of the filing of this patent application, to adequately describe the object or objects of this patent application. However, the description of the object or objects may not be completely applicable to the claims as originally filed in this patent application, as amended during prosecution of this patent application, and as ultimately allowed in any patent issuing from this patent application. Therefore, any statements made relating to the object or objects are not intended to limit the claims in any manner and should not be interpreted as limiting the claims in any manner.

All of the patents, patent applications and publications recited herein, and in the Declaration attached hereto, are hereby incorporated by reference as if set forth in their entirety herein.

The summary is believed, at the time of the filing of this patent application, to adequately summarize this patent application. However, portions or all of the information contained in the summary may not be completely applicable to the claims as originally filed in this patent application, as amended during prosecution of this patent application, and as ultimately allowed in any patent issuing from this patent application. Therefore, any statements made relating to the summary are not intended to limit the claims in any manner and should not be interpreted as limiting the claims in any manner.

It will be understood that any or all the examples of patents, published patent applications, and other documents which are included in this application and including those which are referred to in paragraphs which state "Some examples of . . . which may possibly be used in at least one possible embodiment of the present application . . . " may possibly not be used or useable in any one or more or any embodiments of the application.

The sentence immediately above relates to patents, published patent applications and other documents either incorporated by reference or not incorporated by reference.

All of the patents, patent applications or patent publications, which were cited in the International Search Report dated Dec. 12, 2007, and/or cited elsewhere are hereby incorporated by reference as if set forth in their entirety herein as follows: DE 103 55 183, having the following English translation of the German title "METHOD AND DEVICE FOR HANDLING OBJECTS," published on Jun. 30, 2005; US 2004/208781, having the title "ARTICLE STERILIZING METHODS AND STERILIZING DEVICE," published on Oct. 21, 2004; EP 0 334 288, having the following English translation of the German title "METHOD AND APPARATUS FOR DISPENSING A LIQUID INTO CONTAINERS IN AN ASEPTIC OR STERILE MANNER," published Sep. 27, 1989; WO 01/29528, having the title "MULTIPLE SENSOR IN-LINE CONTAINER INSPECTION," published Apr. 26, 2001; DE 87 00 988, having the German title "PUFFEREINRICHTUNG FÜR FLASCHENBEHANDLUNGSANLAGEN, INSBESONDERE FLASCHENABFÜLLANLAGEN," published on Mar. 5, 1987; and FR 2 576 003, having the following English translation of the French title "METHOD AND INSTALLATION FOR CONTINUOUSLY PERFORMING A PLURALITY OF OPERATIONS ON ARTICLES IN A SINGLE TREATMENT STATION," published on Jul. 18, 1986.

The purpose of incorporating U.S. patents, Foreign patents, publications, etc. is solely to provide additional information relating to technical features of one or more embodiments, which information may not be completely disclosed in the wording in the pages of this application. Words relating to the opinions and judgments of the author and not directly relating to the technical details of the description of the embodiments therein are not incorporated by reference. The words all, always, absolutely, consistently, preferably, guarantee, particularly, constantly, ensure, necessarily, immediately, endlessly, avoid, exactly, continually, expediently, need, must, only, perpetual, precise, perfect, require, requisite, simultaneous, total, unavoidable, and unnecessary, or words substantially equivalent to the above-mentioned words in this sentence, when not used to describe technical features of one or more embodiments, are not considered to be incorporated by reference herein.

The corresponding foreign and international patent publication applications, namely, Federal Republic of Germany Patent Application No. 10 2006 023 764.1, filed on May 20, 2006, having inventors Tobias EULER; Detlef METTE; and Jörg BECKMANN, and DE-OS 10 2006 023 764.1 and DE-PS 10 2006 023 764.1, and International Application No. PCT/EP2007/004434, filed on May 18, 2007, having WIPO Publication No. WO2007/134803 and inventors Tobias EULER; Detlef METTE; and Jörg BECKMANN, are hereby incorporated by reference as if set forth in their entirety herein for the purpose of correcting and explaining any possible misinterpretations of the English translation thereof. In addition, the published equivalents of the above corresponding foreign and international patent publication applications, and other equivalents or corresponding applications, if any, in corresponding cases in the Federal Republic of Germany and elsewhere, and the references and documents cited in any of the documents cited herein, such as the patents, patent applications and publications, are hereby incorporated by reference as if set forth in their entirety herein.

The purpose of incorporating the Foreign equivalent patent application PCT/EP2007/004434 and German Patent Application 10 2006 023 764.1 is solely for the purpose of providing a basis of correction of any wording in the pages of the present application, which may have been mistranslated or misinterpreted by the translator. Words relating to opinions and judgments of the author and not directly relating to the technical details of the description of the embodiments therein are not to be incorporated by reference. The words all, always, absolutely, consistently, preferably, guarantee, particularly, constantly, ensure, necessarily, immediately, endlessly, avoid, exactly, continually, expediently, need, must, only, perpetual, precise, perfect, require, requisite, simultaneous, total, unavoidable, and unnecessary, or words substantially equivalent to the above-mentioned word in this sentence, when not used to describe technical features of one or more embodiments, are not generally considered to be incorporated by reference herein.

Statements made in the original foreign patent applications PCT/EP2007/004434 and DE 10 2006 023 764.1 from which this patent application claims priority which do not have to do with the correction of the translation in this patent application are not to be included in this patent application in the incorporation by reference.

All of the references and documents, cited in any of the documents cited herein, are hereby incorporated by reference as if set forth in their entirety herein. All of the documents cited herein, referred to in the immediately preceding sentence, include all of the patents, patent applications and publications cited anywhere in the present application.

The description of the embodiment or embodiments is believed, at the time of the filing of this patent application, to adequately describe the embodiment or embodiments of this patent application. However, portions of the description of the embodiment or embodiments may not be completely applicable to the claims as originally filed in this patent application, as amended during prosecution of this patent application, and as ultimately allowed in any patent issuing from this patent application. Therefore, any statements made relating to the embodiment or embodiments are not intended to limit the claims in any manner and should not be interpreted as limiting the claims in any manner.

The details in the patents, patent applications and publications may be considered to be incorporable at applicant's option, into the claims during prosecution as further limitations in the claims to patentably distinguish any amended claims from any applied prior art.

The purpose of the title of this patent application is generally to enable the Patent and Trademark Office and the public to determine quickly, from a cursory inspection, the nature of this patent application. The title is believed, at the time of the filing of this patent application, to adequately reflect the general nature of this patent application. However, the title may not be completely applicable to the technical field, the object or objects, the summary, the description of the embodiment or embodiments, and the claims as originally filed in this patent application, as amended during prosecution of this patent application, and as ultimately allowed in any patent issuing from this patent application. Therefore, the title is not intended to limit the claims in any manner and should not be interpreted as limiting the claims in any manner.

The abstract of the disclosure is submitted herewith as required by 37 C.F.R. §1.72(b). As stated in 37 C.F.R. §1.72 (b):

A brief abstract of the technical disclosure in the specification must commence on a separate sheet, preferably following the claims, under the heading "Abstract of the Disclosure." The purpose of the abstract is to enable the Patent and Trademark Office and the public generally to determine quickly from a cursory inspection the nature and gist of the technical disclosure. The abstract shall not be used for interpreting the scope of the claims.

Therefore, any statements made relating to the abstract are not intended to limit the claims in any manner and should not be interpreted as limiting the claims in any manner.

The embodiments of the invention described herein above in the context of the preferred embodiments are not to be taken as limiting the embodiments of the invention to all of the provided details thereof, since modifications and variations thereof may be made without departing from the spirit and scope of the embodiments of the invention.

AT LEAST PARTIAL NOMENCLATURE

1 Machine
2 Bottle
2.1 Bottle mouth
2.2 Bottle flange
3 Sterilizer
4, 5 Activator
6 Conveyor
7 Inlet starwheel
8 Rotor
9 Bottle or container carrier
10 Treatment head
11 Treatment tube
12, 13 Starwheel
14 Rotor
15, 16 Starwheel
17 Rotor
18 Outlet starwheel
19 Conveyor
20, 21, 22, 22' Temperature sensor
23 Electronic measurement and control unit
24 Temperature sensor
SP Start position
SP', SP" Shift of the start position
A, B, C Direction of rotor rotation
EP End position

What is claimed is:

1. A method of treating containers with at least one sterilization medium, said method comprising the steps of:
   moving a container on a rotor along a movement path about a rotational axis of said rotor over an angular distance;
   beginning a treatment procedure of said container by introducing at least one sterilization medium into said container upon said container being disposed at a first position on the movement path;
   terminating said treatment procedure upon said container being disposed at a second position on the movement path;
   measuring a temperature of said container after termination of said treatment procedure;
   determining if the measured container temperature lies within a predetermined range of temperature; and
   changing the length of the portion of the movement path between said first position and said second position upon determining that the measured container temperature lies outside the predetermined range of temperature, and thereby changing the treatment procedure for subsequent containers, such that, after said subsequent containers have been treated according to the changed treatment procedure, the temperatures of said subsequent containers lie within the predetermined range of temperature.

2. The method according to claim 1, wherein said step of changing the length of the portion of the movement path between said first position and said second position comprises utilizing at least one of: an open-loop control action and a closed-loop control action.

3. The method according to claim 2, wherein at least one of (A) to (P):
   (A) said method further comprises moving said containers along the portion of the movement path between said first position and said second position while conducting said treatment procedure; and
   said first position comprises a start position and said second position comprises an end position for treatment of containers;
   (B) the portion of the movement path in which containers are to be treated comprises a treatment path; and
   the length of said treatment path can be modified by open or closed-loop temperature control by comparing the measured container temperature as the actual value to the reference temperature;
   (C) the portion of the movement path in which containers are to be treated comprises a treatment path; and
   the length of said treatment path can be modified as a function of operating parameters comprising at least one of: the number of containers treated per unit time or machine speed, and/or the type and/or size of the containers, and/or the ambient temperature, and/or moisture;
   (D) said method further comprises moving said containers along the portion of the movement path between said first position and said second position while conducting said treatment procedure;
   said first position comprises a start position and said second position comprises an end position for treatment of containers;
   the portion of the movement path in which containers are to be treated comprises a treatment path; and
   said treatment path is modified by modifying at least one of:
   said treatment start position and said treatment end position;
   (E) said method further comprises moving said containers along the portion of the movement path between said first position and said second position while conducting said treatment procedure;
   said first position comprises a start position and said second position comprises an end position for treatment of containers; and
   said treatment end position is set on the basis of operating parameters, and said treatment start position is modified by temperature control;
   (F) said method further comprises moving said containers along the portion of the movement path between said first position and said second position while conducting said treatment procedure;
   said first position comprises a start position and said second position comprises an end position for treatment of containers; and
   said treatment start position is set on the basis of operating parameters, said treatment end position is modified by temperature control;
   (G) the portion of the movement path in which containers are to be treated comprises a treatment path; and
   the container temperature is measured either at the end of said treatment path or immediately downstream of said treatment path;
   (H) the portion of the movement path in which containers are to be treated comprises a treatment path; and
   at least two treatment paths are arranged sequentially in the direction of transport of the containers, and that the length of at least one treatment path can be modified by temperature control and/or as a function of operating parameters;
   (I) the portion of the movement path in which containers are to be treated comprises a treatment path;
   at least two treatment paths are arranged sequentially in the direction of transport of the containers, and that the length of at least one treatment path can be modified by temperature control and/or as a function of operating parameters; and
   the temperature of the containers is measured at the end of each treatment path and or downstream of the end of each treatment path;
   (J) said method comprises the use of multiple rotors arranged in sequence in the direction of transport to form a transport line;
   (K) the portion of the movement path in which containers are to be treated comprises a treatment path;
   at least two treatment paths are arranged sequentially in the direction of transport of the containers, and that the length of at least one treatment path can be modified by temperature control and/or as a function of operating parameters; and
   the containers are treated on at least one treatment path with a heated sterilization medium containing hydrogen peroxide or hydrogen peroxide in the form of an aerosol, and with hot air on at least one subsequent treatment path in the direction of transport;
   (L) the portion of the movement path in which containers are to be treated comprises a treatment path; and
   said method comprises the use of at least one temperature sensor associated with the respective treatment path for the measurement or non-contact measurement of the temperature of the respective container moved past the temperature sensor, which at least one temperature sensor comprises at least one of a pyrometer and an infrared thermometer;
   (M) said method comprises the use of multiple rotors arranged in sequence in the direction of transport to form a transport line, and each of said rotors comprises multiple treatment stations configured to receive one container each;

said treatment stations are disposed around the circumference of said rotor, and each of said treatment paths is formed by an angle area of the rotary motion of the rotor; and said treatment stations each comprise a container carrier and a treatment head, which are controlled by a measurement and control unit as a function of the actual measured temperature of the container and the reference temperature;

(N) the portion of the movement path in which containers are to be treated comprises a treatment path; and said method comprises the use of a transport line with three treatment paths arranged in sequence in the direction of transport of the containers, of which a first treatment path is for treatment with the sterilization medium containing hydrogen peroxide and the two subsequent treatment paths are for treatment with hot air;

(O) said at least one sterilization medium comprises at least one chemical sterilization medium; and (P) said at least one sterilization medium comprises at least one chemical sterilization medium; and said method comprises treating empty containers by introducing said at least one chemical sterilization medium into the containers.

4. The method according to claim 2, wherein:

said method further comprises moving said containers along the portion of the movement path between said first position and said second position while conducting said treatment procedure; and said first position comprises a start position and said second position comprises an end position for treatment of containers.

5. The method according to claim 4, wherein:

the portion of the movement path in which containers are to be treated comprises a treatment path; and the length of said treatment path can be modified by open or closed-loop temperature control by comparing the measured container temperature as the actual value to the reference temperature.

6. The method according to claim 5, wherein the length of said treatment path can be modified as a function of operating parameters comprising at least one of: the number of containers treated per unit time or machine speed, and/or the type and/or size of the containers, and/or the ambient temperature, and/or moisture.

7. The method according to claim 6, wherein said treatment path is modified by modifying at least one of: said treatment start position and said treatment end position.

8. The method according to claim 7, wherein one of (A) and (B):

(A) said treatment end position is set on the basis of operating parameters, and said treatment start position is modified by temperature control; and (B) said treatment start position is set on the basis of operating parameters, said treatment end position is modified by temperature control.

9. The method according to claim 8, wherein the container temperature is measured either at the end of said treatment path or immediately downstream of said treatment path.

10. The method according to claim 9, wherein at least two treatment paths are arranged sequentially in the direction of transport of the containers, and that the length of at least one treatment path can be modified by temperature control and/or as a function of operating parameters.

11. The method according to claim 10, wherein the temperature of the containers is measured at the end of each treatment path and or downstream of the end of each treatment path.

12. The method according to claim 11, wherein said method comprises the use of multiple rotors arranged in sequence in the direction of transport to form a transport line.

13. The method according to claim 12, wherein the containers are treated on at least one treatment path with a heated sterilization medium containing hydrogen peroxide or hydrogen peroxide in the form of an aerosol, and with hot air on at least one subsequent treatment path in the direction of transport.

14. The method according to claim 13, wherein said method comprises the use of at least one temperature sensor associated with the respective treatment path for the measurement or non-contact measurement of the temperature of the respective container moved past the temperature sensor, which at least one temperature sensor comprises at least one of a pyrometer and an infrared thermometer.

15. The method according to claim 14, wherein each of said rotors comprises multiple treatment stations configured to receive one container each.

16. The method according to claim 15, wherein said treatment stations are disposed around the circumference of said rotor, and each of said treatment paths is formed by an angle area of the rotary motion of the rotor.

17. The method according to claim 16, wherein the treatment stations each comprise a container carrier and a treatment head, which are controlled by a measurement and control unit as a function of the actual measured temperature of the container and the reference temperature.

18. The method according to claim 17, wherein said method comprises the use of a transport line with three treatment paths arranged in sequence in the direction of transport of the containers, of which a first treatment path is for treatment with the sterilization medium containing hydrogen peroxide and the two subsequent treatment paths are for treatment with hot air.

19. The method according to claim 18, wherein said at least one sterilization medium comprises at least one chemical sterilization medium.

20. The method according to claim 18, wherein:

said at least one sterilization medium comprises at least one chemical sterilization medium; and said method comprises treating empty containers by introducing said at least one chemical sterilization medium into the containers.

* * * * *